United States Patent [19]

Roberts

[11] Patent Number: 4,668,624
[45] Date of Patent: May 26, 1987

[54] PROTEIN TRANSLATION METHOD

[75] Inventor: Bryan E. Roberts, Arlington Heights, Mass.

[73] Assignee: E.I. Du Pont de Nemours and Company, Wilmington, Del.

[21] Appl. No.: 16,292

[22] Filed: Feb. 28, 1979

[51] Int. Cl.[4] .................. C12P 21/00; C12Q 1/68; C12N 1/00
[52] U.S. Cl. ...................... 435/68; 435/6; 435/317; 435/810; 935/20; 935/21; 935/76
[58] Field of Search ............. 435/6, 68, 70, 71, 296, 435/810

[56] References Cited

U.S. PATENT DOCUMENTS 3,809,616  5/1974  Schmitt et al. ............... 435/810
3,899,298  8/1975  Szczesniak .................. 435/810

OTHER PUBLICATIONS

Pelham et al., Eur. J. Biochem. 67, 247–256 (1976).
Skup et al., Nucleic Acids Research, vol. 4, No. 10, pp. 3581–3587 (Oct. 1977).
Villa-Komaroff et al., Methods in Enzymology, vol. XXX, pp. 709–746.
Lodish, Ann. Rev. Biochem. 45, 39–72 (1976).
McDowell et al., Proc. Nat. Acad. Sci. U.S.A., vol. 69, No. 9, pp. 2649–2653 (Sep. 1972).
Sampson et al., Biochemistry, vol. 11, No. 19, pp. 3636–3640 (1972).
London et al., Federation Proceedings, vol. 35, No. 11, pp. 2218–2222 (Sep. 1976).

Primary Examiner—Alvin E. Tanenholtz

[57] ABSTRACT

An improved method for in vitro synthesis of protein by in vivo processes in an extract from a living organism and containing endogenous ribosomes and endogenous transfer RNA, primarily from endogenous amino acids in said extract primarily by the use of a predetermined exogenous messenger ribonucleic acid (mRNA).

An improved method of assaying such a synthesis by the use of a labelled amino acid, which is present during said synthesis and is incorporated into said protein.

A kit for carrying out such synthesis and assay comprising a vial of substantially prokaryotic and eukaryotic cell-free extract from a living organism containing endogenous ribosomes, endogenous transfer RNA and endogenous amino acids, a vial containing translation cocktail for promoting the synthesis, and a vial containing control messenger RNA.

6 Claims, 2 Drawing Figures

PROTEIN TRANSLATION METHOD

BACKGROUND OF THE INVENTION

1. Field of the Invention

This invention relates to an improved method for in vitro protein synthesis from a substantially prokaryotic and eukaryotic cell-free extract.

It also relates to an improved method of assaying such synthesis.

It also relates to a kit which includes a vial containing substantially prokaryotic and eukaryotic cell-free extract, a vial containing a translation cocktail, and a vial containing a control messenger ribonucleic acid (mRNA).

2. Description of the Prior Art

The conversion of amino acids into protein involves a complicated process involving a number of different components. Genetic information is carried within a cell by a substance known as deoxyribonucleic acid (DNA). DNA is a nucleic acid consisting of different nucleic acids arranged in a double helix chain with the order of attachment determining the genetic code the DNA contains. In a eukaroytic cell, the DNA is contained within the visibly evident nucleus contained within such a cell. In a prokaryotic cell, the DNA is scattered about within the entire cell since such a cell does not have a true nucleus. By a process called transcription, the DNA causes the formation of messenger ribonucleic acid (mRNA), an RNA fraction of intermediate molecular weight which transmits information from DNA to the protein-forming system of the cell. In the case of a eukaryotic cell, this involves the migration of the mRNA through the wall of the nucleus into the cytoplasm of the cell. The mRNA so produced is then picked up by a ribosome, a ribonucleoprotein particle found in the cytoplasm, which converts the message received from the mRNA into a specific protein by a process known as translation. Another component involved in translation is transfer ribonucleic acid (tRNA), an RNA fraction of low molecular weight, existing in 20 species, each of which combines with one amino acid species, transferring it within the cytoplasm to the ribosome. The message from the DNA is contained in mRNA in units known as codons which are three nucleic acid segments which request a particular amino acid depending upon their sequence. The ribosome reads the codon of the mRNA and selects the appropriate tRNA by matching that codon with a tRNA having the complementary anti-condon. The particular amino acid carried by that tRNA is then attached by the ribosome to the end of the growing peptide chain. Thus by sequentially reading the mRNA chain, the ribosome forms a chain of amino acids into a complete protein.

In studying the process by which proteins are formed by living organisms it was determined that research would be aided if the aforesaid protein synthesis could be performed in vitro.

Such methods of synthesizing proteins in vitro are well known in the prior art. For example, see Weissback, H. and Ochoa, S., Ann. Rev. Biochem., 45, 191 (1976); Lucas-Lenard, J. and Lipmann, F., Ann. Rev. Biochem., 40, 409 (1971); Haselkorn, R., and Rothman-Denes, L. B., Ann. Rev. Biochem., 42, 397 (1973); Lucas-Lenard, J. and Beres, L., the Enzymes, 10, 53 (1974); and Ochoa, S. and Mazumder, R., the Enzymes, 10, 1 (1974), all incorporated herein by reference.

In principle, protein synthesis can be regulated at many different levels; from preferential replication of the gene and transcription of the gene into RNA to processing RNA and final protein synthesis. Much remains to be learned about the agents and mechanisms which might be involved in protein synthesis.

One area of protein synthesis which has received a great deal of attention has been translation. There has been a great deal of discussion as to whether different cells differ in their ability to translate different mRNAs. It has been found, in general, that mRNAs from one cell type can be translated efficiently in cell extracts, or intact cells, of a different type without definite requirements for specific factors or other components.

Numerous eukaryotic and prokaryotic cell-free systems efficiently (and faithfully) translate messenger RNAs from viral or eukaryotic origin. In vitro translation systems have been reported for Krebs II ascites tumor, rat and mouse liver, HeLa cells, mouse L cells, Chinese hamster ovary (CHO) cells, other mammalian cells, reticulocytes, wheat germ, rye embryo and other sources. These systems can all be used in assaying RNA molecules for messenger activity. The main disadvantage to the study of mechanisms of translation in vitro is the fact that some of the extracts show high levels of endogenous protein synthesizing activity, i.e. experimental mRNA added to such systems for study must compete with the pre-existing (endogenous) mRNA of the cells from which the extract was produced.

The preparation of an extract efficient in translating in vitro exogenously added mRNA from a wide variety of cells is a potentially useful tool in the study of specificity and control of translation. For example, the rabbit reticulocyte lysate system is reported to contain all factors required for the translation of any eukaryotic mRNA. A reticulocyte is a cell in an intermediate stage in the production of red blood cells from bone marrow cells. Because it has already extruded its nucleus and thus its DNA, it causes less competition from endogenous mRNA produced by the DNA when assaying exogenous mRNA. Unfractionated reticulocyte lysate preparations can be used in prokaryotic and eukaryotic cell-free protein synthesis systems. However, such preparations contain already produced endogenous mRNA, and added mRNA can only be translated to the extent that it can compete with the endogenous mRNA. Treatment of reticulocyte preparations with the enzyme micrococcal nuclease effectively inactivates endogenous mRNA, yet retains activity of other components required for protein synthesis. An example of such a treatment is described in Pelham, H. R. B. and Jackson, R. J., "An Efficient mRNA-Dependent Translation System from Reticulocyte Lysates", Eur. J. Biochem., 67, 247 (1967), incorporated herein by reference. Using this in vitro mRNA-dependent translation system, the mechanisms of protein synthesis, the screening of recombinant DNA and the locating of protein coding regions within eukaryotic or viral DNA can be studied.

Once such prokaryotic and eukaryotic cell-free extract had been prepared, it was combined with the desired experimental exogenous mRNA, tracer and translation cocktail and mixed throughly. The tracer was any of the amino acids expected to be incorporated into the protein by the translation process which was labelled in a suitable manner, e.g. by radioactivity, so that its percentage of incorporation into the protein produced could be determined. The translation cocktail typically consisted of the various components to promote the translation process such as a stabilizer for the tracer, buffer to maintain the system at basically neutral pH, the biochemical energy supply required for the translation process, and amino acids expected to be employed in the translation process other than that employed as the tracer. This mixture was then allowed to incubate for a sufficient period of time, followed by separation of the labelled protein from the remainder of the solution by standard methods well known in the art, such as precipitation using trichloroacetic acid, etc. This separation was followed by methods of analysis well known in the prior art, such as polyacrylamide gel electrophoresis, immunoprecipitation, etc.

A number of problems exist in the prior art. For instance, in preparing the translation cocktail, the prior art suggests that all the amino acids present in the protein to be synthesized, other than the one used as the tracer, should be added to the translation cocktail. Preparing such a cocktail is an onerous, expensive, and time-consuming task. Furthermore, once such a cocktail is prepared, it is unusable with tracers other than the one for which it is prepared.

Another problem is the lack of any standard of comparison, when reviewing protein synthesis of another researcher. To make such a comparison necessitates the complete reproduction of the reported research results.

Another disadvantage concerns the lack of any means for determining where a mistake had been made, such as an improperly prepared reagent, etc., when the desired protein is not produced by the exogenous mRNA. The only means for checking a new protein synthesis is to synthesize a known mRNA and repeat the entire experimental procedure to determine whether the exogenous mRNA is defective or whether a mistake in technique or reagents is involved. Synthesizing or isolating a known mRNA and repeating the experimental procedure can take up to several days.

Accordingly, there is a need for a system providing a convenient reference standard for comparing the research of different investigators. Furthermore, there is a need for a system allowing various tracers to be incorporated without requiring the reformulation of the translation cocktail. In addition, a need also exists for a convenient and readily available model system for use in trouble-shooting an experimental system when problems arise.

SUMMARY OF THE INVENTION

The present invention comprises an improved method of in vitro synthesis of protein in a substantially prokaryotic and eukaryotic cell-free extract from the ribosomes and amino acids primarily in said extract by the use of an exogenous predetermined mRNA, an improved method of assaying such synthesis, and a kit for carrying out such synthesis and assay comprising a container containing a vial of substantially prokaryotic and eukaryotic cell-free extract, a vial containing translation cocktail for promoting the synthesis, and a vial containing control mRNA. A tracer, preferably a labelled amino acid, is used for assaying the synthesis and is preferably stored in a vial as a part of the kit. Optional components of the kit include a vial containing a source of potassium ion, a vial containing a source of magnesium ion, a vial containing purified water, and a vial containing a plurality of assay test strips made of silica gel impregnated glass fiber paper. In a preferred embodiment, the vials in the kit are substantially free from added amino acids other than the labelled tracer.

In using the kit for protein translation, the experimental exogenous mRNA is added to the extract, cocktail and labelled amino acid to achieve protein synthesis from the amino acids in the extract. The amount of labelled amino acid incorporated into the protein during the synthesis and hence the amount of synthesis of the desired protein is measured by the tracer activity e.g. the radioactivity, of the synthesized protein.

DETAILED DESCRIPTION OF THE INVENTION

Figure 2:
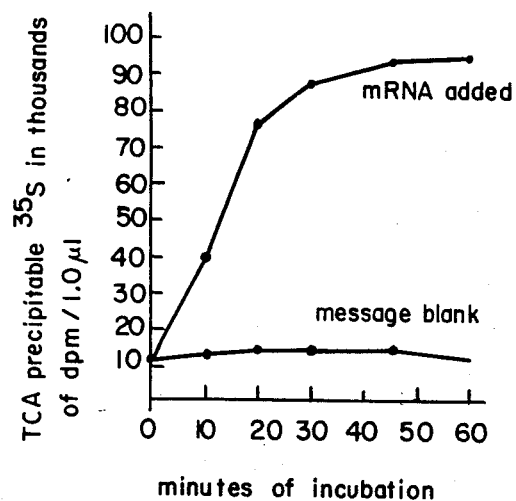
FIG. 2 is a graph showing TCA precipitable $^{35}$S in thousands of dpm/1.0 $\mu$l versus minutes of incubation reported in Example I.

The substantially eukaryotic and prokaryotic cell-free extract can be any of a number of cell extracts known in the prior art such as Krebs II ascites tumor, rat and mouse liver, HeLa cells, mouse L cells, Chinese hamster ovary (CHO) cells, other mammalian cells, reticulocytes, wheat germ, rye embryo, and other similar sources. By substantially eukaryotic and prokaryotic cell-free extract is meant serum from living organisms which is substantially free from DNA either naturally or by treatment to remove DNA-containing material by methods well known in the art. It is preferred that the extract contain as little DNA as possible, although extracts still containing small amounts of DNA are also useful in the present invention. These extracts and their method of manufacture are described in items 7-13, 14, 15, 16, 17, 18-22, 23 and 24 of the list of references in Table I relating to the subject matter of the present invention.

A preferred extract is rabbit reticulocyte lysate which has been treated with micrococcal nuclease to inactivate endogenous mRNA, without substantially impairing the transfer (RNA (tRNA) and ribosomes necessary for efficient translation of externally added mRNA. Micrococcal nuclease requires $Ca^{2+}$ and can be inactivated by adding a chelating agent such as ethyleneglycol-bis (2-aminoethylether)-N,N'-tetracetic acid. Accordingly, it is possible to inactivate the endogenous mRNA but stop the process before the remaining translation portion of the extract has been substantially affected. The reticulocytes are especially useful since the nucleus and hence the mRNA-producing DNA of the cell has already been extruded from the cell in the normal process of forming a red blood cell. With this source of nuclear DNA removed and the endogenous mRNA having been destroyed by enzyme treatment, interference with exogenous mRNA is minimized. The preparation of rabbit reticulocyte lysate for incorporation in the present invention is described in the Pelham and Jackson article, supra.

TABLE I

1. Weissbach, H. and Ochoa, S., Ann. Rcv. Biochem., 45, 191 (1976).
2. Lucas-Lenard, J. and Lipmann, F., Ann. Rcv. Biochem., 40, 409 (1971).
3. Haselkom, R., and Rothman-Denes, L. B., Ann. Rcv. Diochem., 42, 397 (1973).

4. Lucas-Lenard, J. and Beres, L., The Enzymes, 10, 53 (1974).
5. Ochoa, S. and Mazumder, R., The Enzymes, 10, 1 (1974).
6. Lodish, H. F., Ann. Rev. Biochem., 45, 39 (1976).
7. Mathews, M. B., Osborn, M. and Lingrel, J. B., Nature New Biol., 233, 206 (1971).
8. Housman, D., Pemberton, R. and Taber, R., Proc. Natl. Acad. Sci. USA, 68, 2716 (1971).
9. Mathews, M. B., Osborn, M., Berns, A. J. M. and Blocmendal, H., Nature New Biol., 236, 5 (1972).
10. Brownlee, C. G., Harrison, T. M., Mathews, M. B. and Milstein, C., FEBS Letters, 23, 244 (1972).
11. McDowell, M. J., Joklik, W. K., Villa-Komaroff, L., and Lodish, H. F., Proc. Natl. Acad. Sci., USA, 69, 2649 (1972).
12. Kerr, I. M., Brown, R. E. and Tovell, D. R., J. Virol., 10, 73 (1972).
13. Swan, D., Aviv, H. and Leder, P., Proc. Natl. Acad. Sci., USA, 69, 1967 (1972).
14. Sampson, J., Mathews, M. B., Osborn, M. and Borghetti, A. F., Biochemistry, 11, 3636 (1972).
15. Sampson, J. and Borghetti, A. F., Nature New Biol., 238, 200 (1972).
16. Skup, D. and Millward, S., Nuclcic Acid Research, 4, 3581 (1977).
17. Villa-Komaroff, L., McDowell, M., Baltimore, D. and Lodish, H. F., Methods Enzymol. 30, 709 (1974).
18. Lockard, R. E. and Lingrel, J. B., Biochem. Biophys. Res. Commun., 37, 204 (1969).
19. Stavnczer, J. and Huang, R. C. C., Nature New Biol. 230, 172 (1971).
20. Berns, A. J., Strous, G. J. A. M. and Blocmendal, HJ., Nature New Biol. 236, 7 (1972).
21. Lodish, H. F., J. Biol. Chem., 246, 7131 (1971).
22. Pelham, H. R. B. and Jackson, R. J., Eur. J. Biochem., 67, 247 (1976).
23. Roberts, B. E. and Paterson, B. M., Proc. Natl. Acad. Sci., USA, 70, 2330 (1973).
24. Carlier, A. R. And Peumans, W. J., Biochem. Biophys. Acta., 447, 436 (1976).
25. Kuchl, W. M., Current Topics in Microbiology and Immunology, 76, (1977).
26. London, U. M., Clemens, M. J., Ranu, R. S., Levin, D. H., Cherbas, L. F. and Ernst, V., Fed. Prod. J5, 2218 (1976).
27. Laemmli, U. K., Nature, 227, 680 (1970).
28. Marcu, K. B., Valbuena, O. and Perry, R. P., Biochemistry, 17, 1723 (1978).
29. Rowe, D. W., Mocn, R. C., Davidson, J. M., Byers, P. H., Bornstein, P. and Palmiter, R. D., Biochemistry, 17, 1581 (1978).
30. Patterson, B. M. and Bishop, J. O., Cell, 12, 751 (1977).
31. Lewis, J. B., Atkins, J. F., Anderson, C. W., Baum, P. R. and Gesteland, R. F., Proc. Nat'l, Acnd. Sci., 72, 1344 (1975).
32. Palmiter, R. D., Gagnon, J., Ericsson, J. H. and Walsh, K. A., J. Biol. Chem., 252, 6386 1977).

It is also desired to add hemin and creatine kinase to the extract. Hemin is the chloride of heme which is the nonamino acid portion of hemoglobin consisting of ferrous iron bound to proto-porphyrin. Hemin has been found to inhibit an unknown factor which interferes with the process of protein synthesis. Together, creatine kinase and creatine phosphate comprise a known enzyme system for generating biochemical energy for the translation process. Creatine phosphate, also known as phosphocreatine, is a storage form of high-energy phosphate. Creatine kinase is an enzyme that catalyzes the release of that stored biochemical energy. It is preferred that one of them be combined with the extract with the other being included as a part of the translation cocktail described below. This insures that translation does not begin until the components are mixed. However, it is also possible to combine the enzyme system in a single component as long as care is taken to keep the temperature below −70° C. and −80° C. Other similar known enzyme systems generating usable biochemical energy can also be incorporated in the present invention. To extend the useful life of the extract it is desirable to maintain it at −70° C. to −80° C., and preferably at liquid nitrogen temperature. The use of such enzyme systems for this purpose is well known.

The present invention includes a translation cocktail which contains a solution of various components to promote efficient and effective translation. The translation cocktail of the present invention contains the components necessary for the translation process in N-2-hydroxyethyl piperazine N-2-ethane sulfonic acid (HEPES buffer) or other suitable buffer. As discussed above, creatine phosphate is preferably a component of the cocktail, although it is possible to include it as a part of another component of the process. Guanosine triphosphate, another energy-rich compound, is also preferably contained in the cocktail to assist in the formation of the peptide bonds during protein synthesis. Spermidine is an optional component of the system, preferably in the cocktail, which enhances the amount of protein produced. When the tracer used in the system is to be sulfur-containing amino acid such as methionine or cysteine, it is preferred that the translation cocktail also contain dithiothreitol or other thioalcohol as a stabilizer. While the prior art suggests that the cocktail or some other portion of the translation system should be fortified with amino acids other than the one or ones to be used as a tracer, it has been found that the addition of amino acids to the assay system other than the labelled amino acid and the amino acid already in the extract is not required. According to the improved method of synthesis of the present invention and as a preferred embodiment of the present kit, the translation cocktail, as well as the other components of the translation system are essentially free of added amino acids. By eliminating amino acid addition, it is possible to produce a system having a universally useful translation cocktail which can be used with any potential combination of labelled amino acids. Furthermore, the time and effort expended in producing reagents for such a translation system are also reduced. To increase the useful life of stored translation cocktail, it is desirable that storage be at −70° C. to −80° C. Liquid nitrogen storage will typically preserve the cocktail even longer.

A control mRNA is also included as a part of the kit of the present invention. The control mRNA acts as a standard of comparison and thus it is preferred that it be a well known mRNA for which standard data exists. It is advantageous to supply the specifications for the particular mRNA as a part of the kit. By supplying control mRNA with the kit it is possible for the user to check the activity of the other components of the kit thereby reducing the number of variables to be checked should a translation using an experimental exogenous mRNA fail to produce the expected protein or any protein at all. Any known mRNA can be incorporated as a control of the present invention. The particular control mRNA used will vary depending upon which labelled amino acid or combination of labelled amino acids are used as the tracer. For instance, when $^{35}$S-methionine is the tracer, it is preferred that the control mRNA be adenovirus infected HeLa cell mRNA since the spectrum of proteins generated is from over 100,000 daltons to less than 10,000 daltons. This allows the user to check for fidelity of translation by the translation system before testing experimental exogenous mRNAs which produce proteins anywhere within a wide range of different molecular weights. In contrast, a preferred control mRNA for a system employing a tritiated tracer such as $^3$H-leucine is one which produces a narrow spectrum of proteins, due to the less radioactive energy of tritiated tracers. Preferred control mRNAs for systems employing a tritiated tracer are rabbit liver globin mRNA and SV$_{40}$ infected simian cell mRNA.

The tracer is preferably part of the kit in a separate vial but it may be sold separately and used in conjunction with the other kit components during protein translation. A preferred tracer is a radioactively-labelled amino acid. While it is possible to use any of the radionuclides well known in the prior art, those preferred are tritium, $^{14}$C, $^{35}$S, $^{125}$I, and $^{131}$I. For a radio actively-labelled amino acid to be functional in the present invention it must be capable of binding to the appropriate tRNA. Accordingly, $^3$H, $^{14}$C, and $^{35}$S can be used in the present invention simply be replacing the appropriate element with its corresponding isotope. However, in the case of $^{125}$I and $^{131}$I it is necessary to first form a complex between the amino acid to be labelled and the corresponding exogenous tRNA before radio-labelling the amino acid. Because $^{35}$S, $^{125}$I, and $^{131}$I provide a high specific activity label with a $\beta$-emission of suitable energy for rapid autoradiographic detection, preferred amino acids are those containing sulfur, such as methionine and cysteine and those to which an iodine isotope can be bound, such as tyrosine and histidine which have been previously bound to their respective tRNA's forming tyrosyl-tRNA and histidyl-tRNA. Particularly preferred are amino acids having $^{35}$S labels because the isotope effect is negligible compared to the naturally occurring analogues. However, since certain proteins have little or no sulfur-containing amino acids nor amino acids to which $^{125}$I or $^{131}$I can be bound, tritiated amino acids are also useful, preferred tritiated amino acids being $^3$H-leucine and $^3$H-proline. When methionine is the tracer, 2-mercaptoethanol or dithiotreitol is preferably also added to retard decomposition during shipping and storage. Most of the other labelled amino acids other than the above are preferably supplied in acid solution, (e.g., 0.01N HCl) to retard decomposition. Since translation systems are preferably neutral, such acidified amino acids are usually neutralized before use e.g., with NaOH. The concentration of tracer can vary over a wide range, although it is preferred that an excess be present. This excess should remain less than an amount producing significant radiation damage to the newly synthesized protein. Shipping and storage are preferably done at $-70°$ C. to $-80°$ C. to retain the activity of the amino acid.

It is preferred to include as a part of the kit a vial containing a source of potassium ion, preferably as an aqueous solution, and a vial containing a source of magnesium ion, preferably as an aqueous solution. The purpose of the magnesium and potassium ions is to supplement the magnesium and potassium ions already present in the extract. These solutions may be prepared by the user rather than being supplied as a part of the kit. Since translation systems are typically more sensitive to magnesium ion concentration than to potassium ion concentration, it is preferred that the solutions be supplied in separate vials although the two can be combined if desired. Various sources of potassium and magnesium ion can be used in the practice of the present invention. Preferred sources are potassium and magnesium acetate, and potassium and magnesium chloride. Such solutions are preferably stored at $-70°$ C. to $-80°$ C. or colder.

Another potential component of the kit of the present invention is a vial of translation grade water. Translation systems are potentially sensitive to a variety of interferences, including metals, ions, enzymes, etc., which are present in some water supplies. Accordingly, any water used to produce any of the above components, as well as any additional water supplied, should be extremely pure, e.g. deionized and passed through a 0.22 micron millipore filter. Preferably, the water is glass-distilled.

A vial containing transfer RNA (tRNA) may be supplied as a part of the kit to supplement the endogenous tRNA of the extract used. While not generally necessary, the addition of a tRNA, such as mouse liver tRNA to the translation system can result in more efficient production of protein and a higher yield of complete protein chains. Such tRNA should preferably be stored at $-70°$ C. to $-80°$ C.

If desired, there may be included in the kit a vial of a plurality of assay test strips made of silica gel impregnated glass fiber paper for a rapid evaluation of the progress of the protein synthesis during translation, as measured by tracer activity. Such strips should be kept dry, and may be stored at ambient temperature.

The invention will be further clarified by a consideration of the following examples, which are intended to be purely exemplary of the use of the invention.

EXAMPLE I

The following protocol is based on a 25 microliter assay incubation volume. Other incubation volumes might be more suitable for specific investigators. Any changes in the assay volume will necessitate further manipulation of reagents so that proper molarities are maintained. The 25 $\mu$l assay volume is convenient for many of the protein evaluation procedures routinely used; e.g., a small volume of reaction mixture can be applied to a slab polyacrylamide gel electropheresis system for measurement of radioactivity.

The lysate extract and the cocktail were thawed immediately before addition to the translation system. Care was taken to insure that the control mRNA contained no alcohol. In the following example, the mRNA is the control mRNA supplied with the kit. The process was repeated substituting an experimental mRNA (SV$_{40}$ infected simian cell mRNA) for the control with the same result.

A. Preparation

The following materials are required for a translation assay of the control mRNA.

Supplies: (Each provided in a sterile, pyrogen free vial in a typical kit)
    a. control adenovirus infected HeLa Cell mRNA 1.0 $\mu$g/$\mu$l in aqueous solution.

b. rabbit reticulocyte lysate prepared according to Pelham and Jackson, Supra (lysate prepared according to the method of Pelham and Jackson containing 50 μg/ml of creatine kinase, and hemin at a concentration of 25 μM.)
c. translation cocktail (0.35 mM spermidine, 15 mM creatine phosphate, 2 mM dithiothreitol, and 200 μM guanosine triphosphate in 20 mM HEPES buffer)
d. methionine, L-[$^{35}$S]-(680 Ci/mM in aqueous solution containing 50 mM 2-mercaptoethanol)
e. 1.0M potassium acetate in aqueous solution
f. 50 mM magnesium acetate in aqueous solution
g. Water (translation grade)

Supplies: (Provided by investigator)
a. micro test tubes (1.5 ml suggested—tubes of glass, polypropylene, and polyethylene have shown no discernable difference in results)
b. adjustable micropipets
c. ice bath
d. vortex mixer
e. 37° C. incubator
f. microcentrifuge (Eppendorf or equivalent suggested)
g. 10% (w/v) trichloroacetic acid in aqueous solution
h. Whatman 3 mm filter paper
i. ethyl alcohol and acetone
j. scintillation cocktail To minimize possible contamination of the system, gloves (polyethylene, vinyl, etc.) were worn during all phases of the assay procedure.

In the following example, varying quantities of mRNA are to be assayed:

| Tube | mRNA (μl) | Water (μl) | Lysate (μl) | Premix (see below) (μl) |
|---|---|---|---|---|
| 1 | 0.0 | 2.0 | 10.0 | 13.0 |
| 2 | 0.5 | 1.5 | 10.0 | 13.0 |
| 3 | 1.0 | 1.0 | 10.0 | 13.0 |
| 4 | 2.0 | 0.0 | 10.0 | 13.0 |

Since the only variable for this example was the mRNA, the salts (potassium acetate and magnesium acetate), methionine, L-[$^{35}$S]-, and cocktail were combined in a "Premix". Preparation of a "Premix" allowed for greater consistency and accuracy by avoiding multiple addition of the very small aliquots of reagents used.

The "Premix" recipe is shown below. Note that 5 tubes worth of "Premix" were prepared although only 4 tubes were used. This ensured a sufficient overage for complete pipetting.

| Example "Premix" | |
|---|---|
| Per Tube | For 5 Tubes (×5) |
| 8.5 μl methionine, L—[$^{35}$S]— | 42.5 μl |
| 2.0 μl cocktail | 10.0 μl |
| 2.0 μl 1 M potassium acetate | 10.0 μl |
| 0.5 μl 32.5 mM magnesium acetate | 2.5 μl |
| Σ = 13.0 μl | Σ = 65.0 μl |

B. Incorporation

For the assay, the solutions were combined as follows in an ice bath to inhibit degradation of labile components and to ensure that protein synthesis did not commence before all components were added. Each component was carefully pipeted to the bottom of the microtubes as follows:

1. The appropriate mRNA was pipeted into each microtube.
2. The appropriate quantity of water was pipeted into each tube.
3. The "Premix" (13.0 μl in this example) was pipeted into each tube.
4. Ten μl of reticulocyte lysate was pipeted into each tube.
5. The contents of the tubes were quickly vortexed then the tubes were centrifuged in the microcentrifuge to ensure complete mixture of all components at the bottom of each tube. This step was important because small droplets of reaction solution might otherwise have stayed on the walls of the tube and never entered the reaction.
6. A one microliter sample from each tube was spotted onto a two sq. cm square of Whatman 3 mm filter paper.
7. Assay tubes were placed in the 37° C. water bath to begin the incubation.
8. At regular intervals during the incubation, and after the incubation had been completed, a one microliter sample from each tube was spotted onto a two sq. cm square of Whatman 3 mm filter paper.
9. The protein in the sample on each filter paper square produced was precipitated onto the filter paper and thereby separated from the remainder of the contents of the sample by trichloroacetic acid precipitation (explanation below).
10. The radioactivity and thus the amount of protein synthesized in each tube at each point in time was determined by scintillation counting of the precipitated sample on each of the filter paper squares from steps 6 and 8 which had been prepared by treatment in accordance with step 9.

Figure 1:
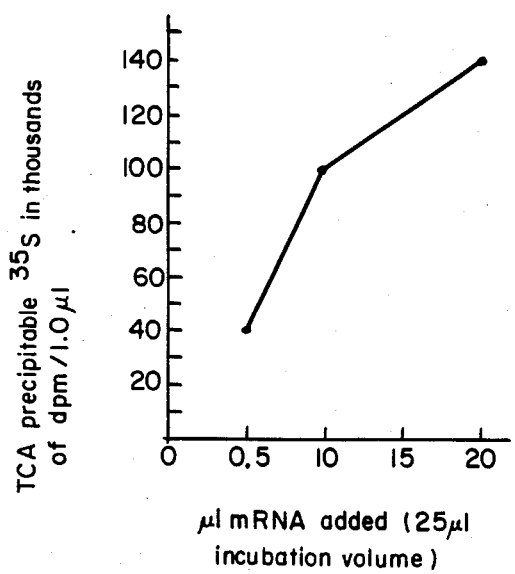
FIG. 1 is a graph showing TCA precipitable $^{35}$S in thousands of dpm/1.0 $\mu$l versus $\mu$l of mRNA added (25 $\mu$l incubation volume) reported in Example I.

FIG. 1 illustrates the amount of protein synthesized using the aforesaid solutions of varying mRNA concentration and an incubation time of one hour. The results are given in TCA precipitable $^{35}$S in thousands of dpm/1.0 microliter incubation mixture versus the number of microliters of mRNA added. The term "dpm" stands for "disintegrations per minute" and is a calculated measure of radioactivity arrived at by multiplying the cpm's measured times the efficiency of the scintillation equipment and the known activity of the particular label such as $^{35}$S to give an indication of the actual amount of label incorporated into the protein. The results for a constant amount of mRNA at various times over a period of one hour are illustrated in FIG. 2. As can be seen in FIG. 2, a minute amount of protein was synthesized in the assay tube containing no exogenous experimental mRNA. This was probably due to endogenous mRNA contained in the lysate. Since the micrococcal nuclease treatment of the lysate described above had to be stopped before all endogenous mRNA was destroyed to prevent significant damage to the ribosomes and tRNA within the lysate, a small amount of competition between the exogenous experimental mRNA and the endogenous mRNA took place and was taken into account in analyzing the results.

C. TCA (Trichloroacetic acid) Precipitation

The 1 microliter samples spotted on filter paper in steps 6 and 8 above provide a qualitative method to determine scintillation counts of the tracer incorporated into the protein synthesized at the time the sample was taken and hence the amount of protein synthesis. The method of separating unreacted amino acids from protein products is a simple 10% (w/v) TCA precipitation. That is, polypeptides are caused to precipitate onto the filter paper while unreacted amino acids were washed away.

As described in steps 6 and 8, a 1 microliter sample was withdrawn from the reaction and spotted onto small squares of Whatman 3 mm paper (1 or 2 cm$^2$) and these were dropped into a one liter beaker of 10% TCA. When all samples were spotted, the TCA was brought to a rolling boil for 10 minutes in a fume hood. At the end of the 10 minutes ice was added to lower the temperature causing the filter papers to drop back down to the bottom of the beaker. The TCA was poured off and the papers were rinsed twice with each of the following: H$_2$O, alcohol, and acetone. The filters were air dried and counted in a liquid scintillation counter with 5-10 ml of scintillation cocktail. The table below summarizes some comparative results (in cpm) for equal aliquots of labeled protein using different scintillation solutions.

| Procedure | Average cpm |
| --- | --- |
| ECONOFLUOR, 10 ml alone | 29,627 |
| 500 µl PROTOSOL, heat at 55° for 30 min., 10 ml ECONOFLUOR | 51,063 |
| BIOFLUOR, 10 ml alone | 24,381 |
| RIAFLUOR, 10 ml alone | 21,803 |
| AQUASOL-2, 10 ml alone | 26,139 |
| Counting conditions: Packard Tri-Carb Model 3385 at 7° C. | |
| Gain: 7% ($^{14}$C counting; Window: 50-1000 | |

The following are sold by New England Nuclear Corporation of Boston, Massachusetts
AQUASOL-2 Universal LSC Cocktail
BIOFLUOR High Efficiency Emulsifier Cocktail
ECONOFLUOR Pre-Mixed Scintillation Solution
PROTOSOL Tissue and Gel Solubilizer
RIAFLUOR Liquid Scintillator for Radioimmunoassay There are many other procedures well known in the prior art used for the evaluation of the protein products synthesized in cell free systems. Some of the most common prior art analytical methods include polyacrylamide gel electrophoresis and methods of immunoprecipitation.

A. Polyacrylamide Gel Electrophoresis

Polyacrylamide gel electrophoretic systems have been used extensively in the analytical separation of the products formed in a cell free translation system. Gel electrophoresis is a well known process in the prior art for separating charged particles by diffusion. The reaction mixture is applied to a slab of gel, each end of the slab is immersed in a separate electrolytic solution and then an electric field is applied across the slab causing the particles, in this case proteins, to move through the medium. The shorter length and lower molecular weight proteins migrate through the gel more rapidly than the longer length and larger molecular weight proteins, forming distinct bands of protein having similar molecular weights and lengths allowing the slab to be cut into segments for detailed analysis of the separate bands. The exact conditions for the electrophoresis system are variable, and, to a large extent determined by the size and nature of the protein products expected. A system which has been useful for the separation of the protein products of the cell-free translation of the mRNA from adenovirus infected HeLa cells is a gradient slab gel from 7.5% to 20% acrylamide (usually a 20×20 cm slab). A gradient slab gel is one in which the concentration of gel increases as the proteins move along the slab providing better resolution of the synthesized protein. Samples are applied and electrophoresis is carried out in a sodium dodecyl sulfate containing buffer. At the end of the electrophoresis, the gels are usually washed in a methanolic TCA solution, soaked in water, soaked in an enhancer solution, washed again and dried. The enhanced gel is then placed against photographic film in order to obtain the autoradiographic banding pattern which visualizes the newly synthesized radioactive proteins. This system is only an example. Other polyacrylamide gel systems can be used and are well known to those skilled in the art.

B. Immunoprecipitation

Immunoprecipitation is a widely used method for the isolation and identification of the products of cell-free translation systems. Immunoprecipitation is a method where a particular protein is isolated from the products of a translation by precipitation. It involves adding to the protein synthesized during translation, the specific antiserum to the protein the individual wants to isolate. Immunoprecipitation provides the advantage of isolation of one specific protein product from translation of a given mRNA. This procedure requires the prior knowledge of the nature of the expected protein product. Specific antiserum to the protein must be available for the immunoprecipitation procedures. Such procedures are well known to those skilled in the art.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

I claim:

1. A method of in vitro synthesis of protein in a translation system comprising synthesizing proteins in a substantially prokaryotic and eukaryotic cell-free extract from cells from a living organism and containing ribosomes, wherein said proteins are synthesized essentially from amino acids endogenous to said extract using a predetermined exogenous messenger RNA.

2. A method of assaying the protein produced by the method of claim 1 comprising carrying out said synthesis in the presence of a tracer which is incorporated in said synthesized protein during said synthesis.

3. The method of claim 2 wherein said tracer is a radioactively-labelled amino acid.

4. The method of claim 3 wherein said amino acid is L-$^{35}$S-methionine or L-$^{3}$H-leucine.

5. The method of claim 3 wherein said tracer is iodinated histidyl-tRNA or iodinated tyrosyl-tRNA.

6. A method for in vitro synthesis of protein comprising synthesizing said protein by in vivo processes in an extract from a living organism containing endogenous ribosomes and endogenous transfer RNA, wherein said protein is synthesized essentially from endogenous amino acids in said extract using a predetermined exogenous messenger RNA.

* * * * *